(12) United States Patent
Johnson

(10) Patent No.: US 9,181,173 B2
(45) Date of Patent: Nov. 10, 2015

(54) SYNTHESIS OF TETRABUTYLAMMONIUM BIS(FLUOROSULFONYL)IMIDE AND RELATED SALTS

(71) Applicant: Trinapco, Inc., Oakland, CA (US)

(72) Inventor: Martin Reid Johnson, Oakland, CA (US)

(73) Assignee: TRINAPCO, INC., Oakland, CA (US)

( * ) Notice: Subject to any disclaimer, the term of this patent is extended or adjusted under 35 U.S.C. 154(b) by 126 days.

(21) Appl. No.: 14/081,817

(22) Filed: Nov. 15, 2013

(65) Prior Publication Data

US 2014/0142338 A1    May 22, 2014

Related U.S. Application Data

(60) Provisional application No. 61/727,616, filed on Nov. 16, 2012.

(51) Int. Cl.
  *C07C 209/68* (2006.01)
  *C07C 211/03* (2006.01)
  *C01B 21/086* (2006.01)

(52) U.S. Cl.
  CPC ............. *C07C 209/68* (2013.01); *C01B 21/086* (2013.01)

(58) Field of Classification Search
  CPC ........................... C07C 209/68; C07C 211/03
  See application file for complete search history.

(56) References Cited

U.S. PATENT DOCUMENTS

| | | | |
|---|---|---|---|
| 2,130,038 A | 9/1938 | Schrader et al. | |
| 3,379,509 A | 4/1968 | Appel | |
| 3,387,946 A | 6/1968 | Appel | |
| 3,411,889 A | 11/1968 | Kopec | |
| 3,418,088 A | 12/1968 | Shozda | |
| 5,072,040 A | 12/1991 | Armand | |
| 5,256,821 A | 10/1993 | Armand | |
| 5,723,664 A | 3/1998 | Sakaguchi et al. | |
| 5,874,616 A | 2/1999 | Howells et al. | |
| 6,252,111 B1 | 6/2001 | Sakai et al. | |
| 6,319,428 B1 | 11/2001 | Michot et al. | |
| 6,365,301 B1 | 4/2002 | Michot et al. | |
| 6,452,048 B2 | 9/2002 | Yonezawa et al. | |
| 6,682,855 B2 | 1/2004 | Michot et al. | |

(Continued)

FOREIGN PATENT DOCUMENTS

| | | |
|---|---|---|
| CA | 2826547 A1 | 9/2012 |
| DE | 1199244 | 8/1965 |
| JP | 2011144086 A3 | 7/2011 |
| WO | 2010140580 A1 | 12/2010 |
| WO | 2011149095 A1 | 12/2011 |
| WO | 2012020513 A1 | 2/2012 |

OTHER PUBLICATIONS

Search Report and Written Opinion from corresponding PCT Application No. PCT/US2013/070410.

(Continued)

*Primary Examiner* — Sudhakar Katakam
*Assistant Examiner* — Jennifer C Sawyer
(74) *Attorney, Agent, or Firm* — Duane Morris LLP

(57) ABSTRACT

The present invention is directed to methods comprising adding ammonia, either as an ammonium salt or as a gas at pressures below 0.01 MPa, to a sulfuryl fluoride solution to form the anion of bis(fluorosulfonyl)amine under conditions well suited for large-scale production. The bis(fluorosulfonyl)amine so produced can be isolated by methods described in the prior art, or isolated as an organic ion pair, such as an alkylammonium solid salt, or as an ionic liquid.

20 Claims, 1 Drawing Sheet

(56) References Cited

U.S. PATENT DOCUMENTS

| | | | |
|---|---|---|---|
| 8,134,027 | B2 | 3/2012 | Okumura et al. |
| 8,377,406 | B1 | 2/2013 | Singh et al. |
| 2004/0097757 | A1 | 5/2004 | Cernik et al. |
| 2007/0043231 | A1 | 2/2007 | Hammami et al. |
| 2011/0034716 | A1 | 2/2011 | Okumura et al. |
| 2011/0034732 | A1 | 2/2011 | Ishii et al. |
| 2012/0009113 | A1 | 1/2012 | Honda et al. |
| 2012/0014859 | A1 | 1/2012 | Honda et al. |
| 2012/0020867 | A1 | 1/2012 | Morinaka et al. |
| 2012/0070358 | A1 | 3/2012 | Morinaka et al. |
| 2012/0245386 | A1 | 9/2012 | Johnson |

OTHER PUBLICATIONS

Ruff "Sulfur Oxyfluoride Derivatives.II" Inorganic Chemistry [Online] 1965, 4(4), pp. 567-570.

Tsuzuki et al. "Origin of the Low-Viscosity of [emim][FSO2)2N] Ionic Liquid and Its Lithium Salt Mixture; Experimental and Theoretical Study of Self-Diffusion Coefficients, Coductivities, and Intermolecular Interactions" Journal of Physical Chemistry B [Online] 2010,114, pp. 16329-16336.

R. Appel et al., Uber die Umsetzung von Disulfurylflorid, S2O5F2, mit Ammoniak und Diathylamin. Zeitschriftfur anorganische und allgemeine chemie 1961, vol. 310, No. 1-2, pp. 9093; p. 91-93.

Emeleus, H.J. And J.F. Wood, 442. The preparation and reactions of carbonyl and sulphuryl fluorides and chlorofluorides. Journal of the Chemical Society (Resumed), 1948: p. 2183-2188. DOI: 10.1039/JR9480002183.

Appel, R. And G. Eisenhauer, Uber die Umsetzung von Disulfurylfluorid, S2O5F2, mit Ammoniak und Diathylamin. Zeitschrift für anorganische und allgemeine Chemie, 1961. 310(1-2): p. 90-93. DOI: 10.1002/zaac.19613100112.

Appel, R. And H. Rittersbacher, Über die Reaktion von Sulfuryl-diisocyanat mit Halogeno-schwefelsauren. Ein einfaches Verfahren zur Herstellung von Fluorsulfonylisocyanat und Imido-bisschwefelsaurefluorid. Chemische Berichte, 1964. 97(3): p. 849-851. DOI: 10.1002/cber.19640970330.

Ruff J.K., The Imidodisulfuryl Fluoride Ion. Inorganic Chemistry, 1965. 4(10): p. 1446-1449. DOI: 10.1021/ic50032a019.

Ruff, J.K., et al., Imidodisulfuryl Fluoride, Cesium Imidodisulfuryl Fluoride, and Fluoroimidodisulfuryl Fluoride: [<I>Imidobis(Sulfuryl Fluoride), Cesium Imidobis(Sulfuryl Fluoride), and Fluoroirnidobis(Sulfuryl Fluoride</I>)], in Inorganic Syntheses, L.J. William, Editor. 1968. p. 138-143.

Vij, A., et al., Some fluorine-containing nitrogen acids and their derivatives. Coordination Chemistry Reviews, 1997. 158: p. 413-432. DOI: 10.1016/s0010-8545(97)90069-2.

Krumm, B., et al., Synthesis of Poly- and the First Perfluoroalkyl-N(SO2F)2 Derivatives: Improved Methods for the Preparation of XN(SO2F)2 (X = H, Cl) and Single-Crystal Diffraction Studies of HN(SO2C1)2, HN(SO2F)2, and CF3CH2N(SO2F)2†. Inorganic Chemistry, 1998. 37(24): p. 6295-6303. DOI: 10.1021/ic9800031.

Beran, M. And J. Prihoda, A New Method of the Preparation of Imido-bis(sulfuric acid) Dihalogenide, (F, Cl), and the Potassium Salt of Imido-bis(sulfuric acid) Difluoride. Zeitschrift für anorganische and allgemeine Chemie, 2005. 631(1): p. 55-59. DOI: 10.1002/zaac.200400325.

Beran, M., et al., A new route to the syntheses of alkali metal bis(fluorosulfuryl)imides: Crystal structure of LiN(SO2F)2. Polyhedron, 2006. 25(6): p. 1292-1298. DOI: 10.1016/j.poly.2005.09.017.

Huang, J. And A. F. Hollenkamp, Thermal Behavior of Ionic Liquids Containing the FSI Anion and the Li+ Cation. The Journal of Physical Chemistry C, 2010. 114(49): p. 21840-21847. DOI: 10.1021/jp107740p.

Kim, G.T., et al., UV cross-linked, lithium-conducting ternary polymer electrolytes containing ionic liquids. Journal of Power Sources, 2010. In Press, Corrected Proof. DOI: 10.1016/j.jpowsour.2009.10.079.

Kubota, K. T Nohira, and R. Hagiwara, Thermal Properties of Alkali Bis(fluorosulfonyl)amides and Their Binary . T. Mixtures. Journal of Chemical & Engineering Data, 2010. 55(9): p. 3142-3146. DOI: 10.1021/je9010932.

Lewandowski, A.P., et al., Cycling and rate performance of Li-LiFePO4 cells in mixed FSI-TFSI room temperature ionic liquids. Journal of Power Sources, 2010. 195(7): p. 2029-2035. DOI: 10.1016/j.jpowsour.2009.10.059.

Han, H.-B., et al., Lithium bis(fluorosulfonyl)imide (LiFSI) as conducting salt for nonaqueous liquid electrolytes for lithium-ion batteries: Physicochemical and electrochemical properties. Journal of Power Sources, 2011. 196(7): p. 3623-3632. DOI: 10.1016/j.jpowsour.2010.12.040.

Lifei, L., et al., Transport and Electrochemical Properties and Spectral Features of Non-Aqueous Electrolytes Containing LiFSI in Linear Carbonate Solvents. Journal of the Electrochemical Society, 2011. 158(2): p. A74-A82. DOI: 10.114911.3514705.

Marom, R., et al., A review of advanced and practical lithium battery materials. Journal of Materials Chemistry, 2011. 21(27): p. 9938-9954. DOI: 10.1039/c0jm04225k.

Nádherná, M., et al., Lithium bis(fluorosulfonyl)imide-PYR14TFSI ionic liquid electrolyte compatible with graphite. Journal of Power Sources, 2011. 196(18): p. 7700-7706. DOI: 10.1016/j.jpowsour.2011.04.033.

Appel, R. And G. Eisenhauer, Die Synthese des Imidobisschwefelsaurefluorids, HN(SO2F)2. Chemische Berichte, 1962. 95(1): p. 246-248. DOI: 10.1002/cber.19620950139.

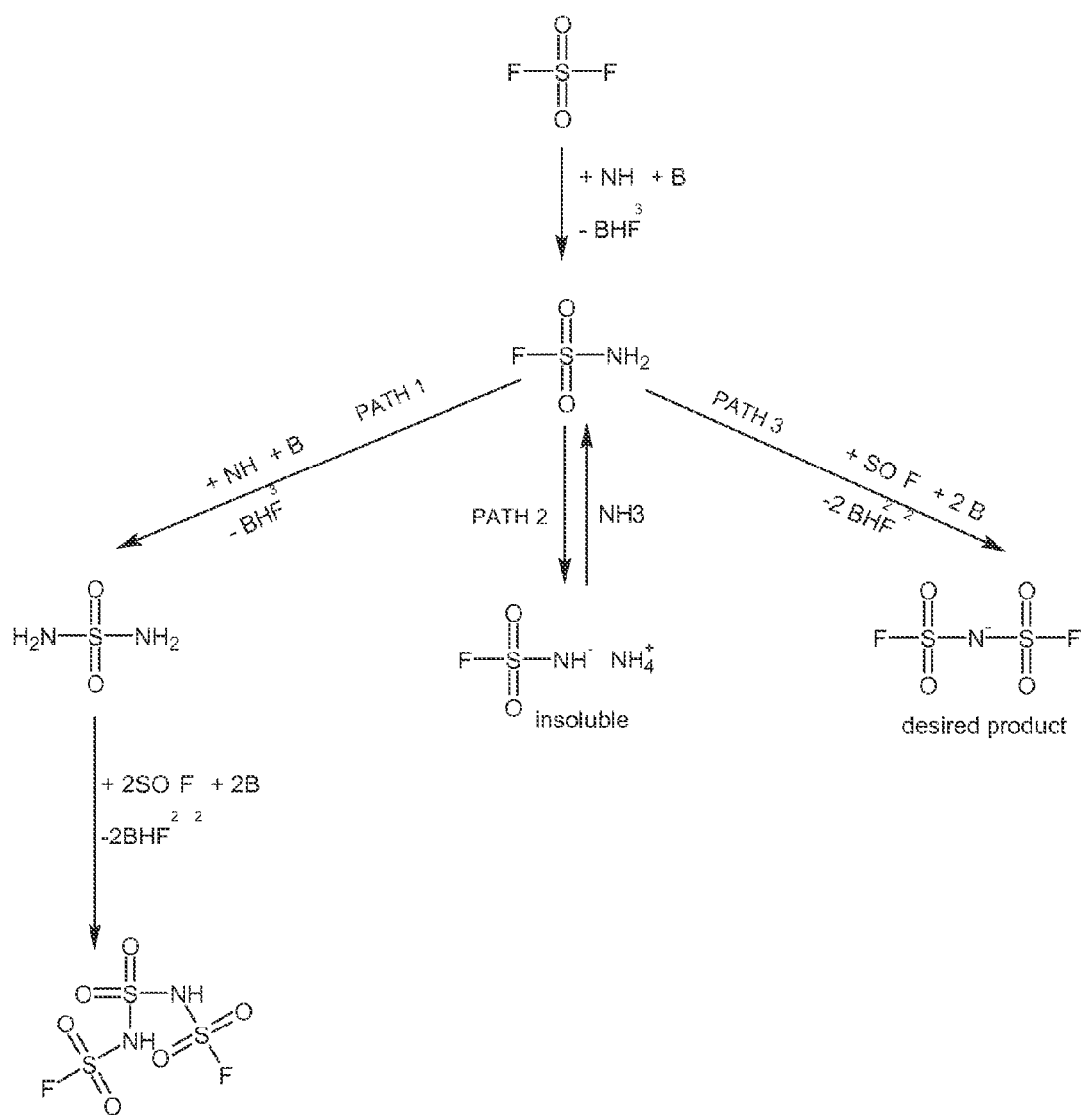

SYNTHESIS OF TETRABUTYLAMMONIUM BIS(FLUOROSULFONYL)IMIDE AND RELATED SALTS

CROSS-REFERENCE TO RELATED APPLICATIONS

This application claims the benefit of U.S. Provisional Patent Application No. 61/727,616, filed Nov. 16, 2012, which is incorporated by reference herein in its entirety.

BACKGROUND OF THE INVENTION

1. Field of the Invention

The present invention is directed to nonobvious improvements in the preparation of tetrabutylammonium bis(fluorosulfonyl)imide, $[Bu_4N]^+[(FSO_2)_2N]^-$, and related salts.

2. Background

Compounds containing bis(fluorosulfonyl)imide $[(FSO_2)_2N]^-$ are useful, for example, as Lewis acid catalysts, ion transport agents, in the fields of organic compound syntheses, electrolytes and the like.

Various methods for synthesizing bis(fluorosulfonyl) amine, and related compounds have been proposed (see, e.g., Ruff, *Inorg. Chem.* 4 (10):1446 (1965); Ruff, *Inorg. Synth. XI:*138 (William, ed., McGraw-Hill Book Co., 1968); Vij et al., *Coord. Chem. Rev.* 158:413 (1997); Krumm et al., *Inorg. Chem.* 37:6295 (1998); Beran et al., *Z. Anorg. Allg. Chem.* 631:55 (2005); U.S. Pat. No. 8,377,406, U.S. Pat. No. 5,723, 664; and U.S. Pat. No. 5,874,616; DE Pat. No. 1 199 244). However, these methods may not be appropriate for industrial scale production either because they provide low yields, or require the formation of, e.g., dangerous intermediates and/or or corrosive/expensive starting materials.

A advances in obtaining $[(FSO_2)_2N]^-$ and its salts were disclosed by Morinaka (US2012/0028067 A1 and US2012/0070358 A1), incorporated by reference herein in their entirety, who treated a solution of $SO_2F_2$ in acetonitrile with ammonia gas, in the presence of an aprotic base, to obtain salts of $[(FSO_2)_2N]^-$ in high yield. As used herein "an aprotic base" has no labile hydrogen atoms. For example, diethylamine is a protic base and triethylamine is an aprotic base. By use of elevated pressure conditions, Morinaka was able to contain $SO_2F_2$ and thereby allow it to react with the ammonia at high concentration.

Those skilled in the art will recognize that Morinaka's processes use reactor pressures above atmospheric. The elevated pressure conditions described by Morinaka are problematic for commercial scale synthesis of $[(FSO_2)_2N]^-$ salts; since large scale synthesis would require large pressurized vessels. Large pressurized vessels for commercial scale synthesis can be cost-prohibitive, compared with lower cost vessels designed for use at atmospheric pressure and below. Additionally, there are increased safety issues which arise from the handling of $SO_2F_2$, at high pressure, which is highly toxic and completely undetectable by the senses or by common forms of measurement. Exposure of $SO_2F_2$ can be fatal to the operator.

Thus, there is a need for an improved synthesis of salts of $[(FSO_2)_2N]^-$, which can be safely and economically scaled up for commercial application.

The present invention is based in part on the discovery that gas-phase reactor fouling occurs under the conditions of Morinaka's process, namely, at pressures above 0.01 MPa. Fouling is a problem which adds to the cost of labor, as the foulant must be cleared between runs. This extends well beyond a simple rinse, as any component whose surface comprises a part of the reactor head space must be disassembled. The foulant is a volatile, toxic, fluoride-containing slag. Even if the components are well cleansed, fouling can cause equipment failure through corrosion and abrasion of, e.g., stir bearings and seals. For industrial scale production of $[(FSO_2)_2N]^-$ salts, operation under conditions that do not foul the reactor, and minimize $SO_2F_2$ leakage hazards, are much preferred.

BRIEF DESCRIPTION OF THE DRAWINGS

FIG. 1 shows a reaction scheme for the reaction of $SO_2F_2$ with $NH_3$.

SUMMARY OF THE INVENTION

One object of the present invention is a process in which the slow and constant infusion of ammonia ($NH_3$) to the head space above a solution of $SO_2F_2$, in the presence of an aprotic base, can be accomplished safely and on a commercial scale at pressures below 0.01 MPa. Yields of $[(FSO_2)_2N]^-$ salts from this process are greater than or equal to those reported by Morinaka. Furthermore, reactor fouling is eliminated by operation at these lower pressures.

Another object of the present invention is a process in which $NH_3$ is added as a salt to $SO_2F_2$, such as by introduction of $NH_3$ as ammonium salt (e.g., $NH_4F$). By addition of a salt of $NH_3$, reactor pressures above 0.01 MPa may be employed safely. Yields are the same as with gas infusion at lower pressure and no fouling occurs.

It is an object of the invention to provide a process for the production of a salt of bis(fluorosulfonyl)imide anion ($M^+_n$ $[(FSO_2)_2N^-]_m$), wherein $M^+$ is a an inorganic or organic cation and n and m are 1-4, comprising:

adding ammonia to a solution of sulfuryl fluoride ($SO_2F_2$) in a solvent in a sealed reactor, in the presence of an aprotic base, while maintaining a pressure inside the sealed reactor below 0.01 MPa (75 Torr), to produce a solution comprising the product ion $[(FSO_2)_2N]^-$ ("FSI");

adding the solution comprising the product ion $[(FSO_2)_2N]^-$ ("FSI") to a solution comprising of a salt of $M^+$ and isolating the resulting salt comprising bis(fluorosulfonyl) imide anion ($[(FSO_2)_2N]^-$).

DETAILED DESCRIPTION OF THE INVENTION

Generally speaking, the reaction of $SO_2F_2$ with $NH_3$ takes place only in liquid solution and not in the gas phase. However, reactor fouling shows that surface reactions can occur. Some of the relevant reactions of $SO_2F_2$ with $NH_3$ are shown in FIG. 1.

The initial reaction of $SO_2F_2$ with $NH_3$ is a vigourous aminodefluorination, giving fluorosulfonamide, $FSO_2NH_2$. $FSO_2NH_2$ may then react in one of several ways: a second aminodefluorination to give sulfamide (path 1), or deprotonation, giving fluorosulfonamidate anion ($FSO_2NH^-$, paths 2 and 3). Dissolved $FSO_2NH^-$ is the intermediate which produces the product of both this and Morinaka's invention. $FSO_2NH^-$ is sufficiently inert so that $FSO_2NH_2$ may be isolated in good yields upon acidification of the intermediate pot (see, for example, PCT patent application WO 2012/028292 A1). $FSO_2NH^-$ undergoes further, slower reaction with $SO_2F_2$ to give $(FSO_2)_2NH$, which rapidly deprotonates to give the product anion $(FSO_2)_2N^-$, isolated as an ion pair.

Use of Ammonia Gas as Reactant

The reaction of $NH_3$ gas with dissolved $SO_2F_2$ is highly exothermic and extremely rapid, and the rate of $NH_3$ gas addition must be carefully controlled. In a preferred embodiment, the $NH_3$ gas is slowly added over a course of at least 90 minutes, or more preferably two hours or longer, to a vigorously stirred $SO_2F_2$ solution. The rate of addition is typically regulated by the rise in temperature above a starting temperature. In some embodiments, the rise in temperature from the starting static temperature is maintained at ±5° C. or less, and more preferably ±2° C. or less during the addition of $NH_3$. Effective cooling of the reactor is required to remove the heat of reaction.

Precision control of $SO_2F_2$ and/or $NH_3$ introduction can be maintained using, e.g., mass flow controllers, caliper gauges, and the like. In some embodiments, the rate of $NH_3$ addition (and/or $SO_2F_2$ addition) is controlled by internal reactor pressure, reactor temperature, or other variable conditions.

The order and rate of addition of $NH_3$ and $SO_2F_2$ can be varied, within limits. There must be a large molar excess of $SO_2F_2$ in the reactor during $NH_3$ addition. For example, $NH_3$ can be added at a continuous rate to a reactor charged with $SO_2F_2$ to 70 Torr (0.0093 MPa), and additional $SO_2F_2$ added portion-wise in a pressure-dependent fashion using, e.g., a gated valve. In a preferred embodiment, both reagents are introduced simultaneously at a controlled rate. For example, additional $SO_2F_2$ can be added when the reactor pressure drops below, e.g., 70 Torr.

The rate of $NH_3$ addition can be varied as a function of the degree of agitation of the reactor contents: better mixing in the reactor allows for more rapid addition of $NH_3$. The rate of $NH_3$ addition should be controlled to reduce the formation of byproducts. For a two-gallon reactor with maximum agitation, a two-hour addition time was sufficient to provide yield of 95% or greater. While nonetheless within the scope of the invention, under similar conditions adding the $NH_3$ at a constant rate over one hour resulted in reduced yield and formation of higher amounts of insoluble byproducts.

Preferably, the aprotic base (B) is capable of remaining dissolved as an ion pair with the anions produced (i.e., $BH^+(FSO_2)_2N^-$, $BH^+FSO_2NH^-$, and $BH^+F^-$). Exemplary non-reactive bases (and many inoperative bases) are described by Morinaka, who did not describe TMPDA, which has been found to be the most useful base for the process. Tertiary alkylamines are preferred bases, more preferably TMPDA. TMPDA enables the highest reactor loads, is inexpensive, and recyclable. TMPDA gives a clear pot liquor, so the reactor can be reused after a simple rinse. TMPDA as a process base yields concentrates which have low melting points and are widely soluble. TMPDA has a moderate boiling point which enables its reuse.

Acceptable solvents include ethers (e.g., diethylether, THF, and the like), nitriles (e.g., acetonitrile, butyronitrile, and the like), esters (e.g., ethyl acetate and the like), halocarbons (e.g., dichloromethane and the like), and tertiary amides (e.g., N,N-dimethylacetamide (DMA), N-methylpyrrolidinone (NMP), tetramethylurea (TMU), dimethylpropyleneurea (DMPU), dimethylethyleneurea, and the like. Solvents with higher polarity are more preferred. Solvents in which $SO_2F_2$ dissolves well are more preferred.

The ratio of $NH_3$ to $SO_2F_2$ in theory is 1:2. Practically, a molar ratio of 1.008:2 has been employed. Higher mole ratios can be employed but offer no advantage, and increase the likelihood of byproduct formation.

The ratio of base to $SO_2F_2$ in theory is 3:2. In practice, with TMPDA a mole ratio of 1.03:1 (equivalent ratio 2.06:1 or about 4:2) gave 85-95% yields. This ratio can be reduced to a level approaching theoretical without substantially affecting the yield, provided the base is stronger than $NH_3$, as is the case with both of the nitrogen atoms in TMPDA.

The amount of solvent depends on the solubility of the products. Low polarity solvents cannot give reactor loads of 1 molal without forming pot solids; most need much lower loads to prevent this from happening. More polar solvents can give loads in excess of 1 molal. With acetonitrile and TMPDA as solvent and base, respectively, loads of 1.1 molal gave a clear liquor and no pot solids. Solids began to form above about 1.1 molal in this solvent/base combination.

$NH_3$ addition at −10° C. and 70 Torr using acetonitrile and TMPDA as solvent and base, respectively, is complete well before one mole equivalent of $SO_2F_2$ has been added, and high yields still obtained (Example 3). This indicates that added $NH_3$ is partly sequestered (i.e., as $NH_4F$) during addition (see FIG. 1). The substoichiometry of added $SO_2F_2$ in Example 3 also indicates that intermediate $FSO_2NH_2$ is partly sequestered, following the reversible path 2 and not the irreversible path 1 under these conditions (see FIG. 1).

At elevated pressures during $NH_3$ addition, fouling occurs. Solids, soaked with solvent and base, form wherever interior surfaces are not liquid-wet. In these reactions at about 0.1 MPa (1 atmosphere) in a 2-gallon (7.57 L) Parr reactor with overhead stirring the head space fouled every time. All of the piping into the head space, the check valves, and the stir assembly fouled. The reactor had to be dismantled and cleaned after each run. The stir assembly could not be easily cleaned and generally failed after three runs, from both abrasion by the foulant and/or swelling of the bearings, and corrosion, i.e. leaching of carbon from the bearings into the foulant. While PTFE ("Teflon™") bearings mitigated the corrosion problem, the abrasion problem persisted.

Fouling only occurs during $NH_3$ addition, and is eliminated by use of reactor pressures below 0.01 Mpa (75 Torr). The reactor pressure may be raised after $NH_3$ addition as fouling is no longer an issue. The pressure may be raised by an increase in temperature, more preferably addition of $SO_2F_2$, or a combination of the two.

Reactor temperature can be dependent on the stage of the reaction and the solvent used, and is dictated to some extent by the vapor pressure of the solvent and base. For example, acetonitrile has a significant vapor pressure above about 10° C. When acetonitrile is used as a solvent, $NH_3$ addition is conducted between −30 and +20° C., preferably −15 to +5° C. Higher boiling solvents and bases may be used at higher temperatures (up to 40° C.) for the $NH_3$ addition, within the scope of this invention. Nonvolatile bases (e.g. polymeric tertiary amines and the like), may be used within the scope of this invention.

If a volatile solvent (e.g., acetonitrile) is used, once the $NH_3$ has been added, the temperature should be raised to +10 to +40° C., more preferably, 24-28° C., and the reactor pressure raised by introduction of $SO_2F_2$ to below 0.1 MPa (750 Torr) in order for the reaction to timely complete (FIG. 1, path 3). Higher pressures may be employed but are best left below atmospheric for safety. In a properly degassed reaction, the endpoint pressure will approach that of the solvent vapor pressure as the $SO_2F_2$ is fully consumed. The contents are then removed from the reactor as a clear liquid.

In a preferred embodiment, the reactor may then be reused without extensive cleaning In a preferred embodiment, the reaction may be performed in its entirety at pressures below 0.01 MPa if a suitably high boiling solvent/base combination is used.

Use of Ammonium Salt as Reactant

In another preferred embodiment of the invention, fouling is suppressed by introduction of $NH_3$ as ammonium salt (e.g., NH$_4$F). An additional equivalent of base is required. In this embodiment, reactor pressure can be greater than 0.1 MPa, and up to about 0.3 MPa, but reactor pressures below 0.1 MPa are preferred for safety. Pressures slightly below atmospheric are most preferred. Ammonium fluoride is preferred over other salts as the byproducts are generally more soluble in the process solvent. For example, while nonetheless within the scope of the invention, e.g. ammonium chloride is less preferred; it gave an insoluble byproduct and a contaminated product (comparative Example 1).

Ammonium fluoride is insoluble in most aprotic organic solvents. Furthermore, conversion of suspended NH$_4$F to free ammonia in the presence of, e.g. TMPDA, is very slow under process conditions, even if finely divided solid is used. This effects slow addition of NH$_3$ to the pot, and prevents any escape of NH$_3$ into the head space. A clear pot liquor is obtained without fouling. Isolated yields of product by this embodiment of the invention are the same as yields obtained with ammonia gas (Examples 1 and 2).

In this embodiment of the invention, temperatures of 0-50° C. may be used, more preferably, 24-28° C.

By use of the above improvements, commercially viable scale-up may be achieved at acceptable cost and improved safety.

The pot liquor obtained from the embodiments of the invention may be treated as described below to isolate the product.

The product ion [(FSO$_2$)$_2$N]$^-$ ("FSI") can be isolated as a metal salt, an organic salt, or other salt. Solid salts are preferred over ionic liquids, which are nonetheless within the scope of the invention. In some embodiments, a C$_1$-C$_5$ tetraalkylammonium salt is used to precipitate the FSI, for example, tetrabutylammonium bromide (Bu$_4$NBr). In some embodiments, quaternary ammonium hydroxides (e.g., Bu$_4$NOH and the like) are preferred. One product, Bu$_4$NFSI, has a melting point of about 99° C. that enables it to be handled under ambient conditions, is insoluble in water, only slightly soluble in cold methanol, and very soluble in hot methanol. Maximum recovery of FSI can be achieved this way to give isolated yields higher than reported by Morinaka. Another salt, Me$_4$N$^+$FSI$^-$ (via Me$_4$NCl), gave an initial precipitate having 10-17 ppm chloride (by ion chromatography), and undetectable amounts of chloride (<10 ppm) after a second recrystallization from distilled water. The recovery of FSI as Me$_4$NFSI is, however, about 10% lower than for Bu$_4$NFSI. Solid alkylammonium salts obtained by this invention are of very high purity, and can be dried to very low water levels.

EXAMPLES

Example 1

A 1-liter, 4-necked roundbottom flask was equipped with a stir egg, gas inlet, pressure-compensated dropping funnel, and a thermometer, and charged with ACS grade ammonium fluoride (16.06 grams, 0.43 moles) and 1-methyl-2-pyrrolidinone (NMP, 462 g). The dropping funnel was charged with 1,3-bis(dimethylamimo)propane (TMPDA, 120 grams, 0.92 mole). The flask was then sealed and evacuated under dynamic vacuum with magnetic stirring, whereupon the TMPDA and NMP both experienced outgassing. After a few seconds at 20 Torr, the vacuum was halted and the flask filled with SO$_2$F$_2$ gas until a stable pressure of 700 Torr was reached. The TMPDA was then dropped into the stirred flask contents over a period of 10 seconds and the flask contents stirred in a 25° C. water bath with continuous addition of SO$_2$F$_2$ at the set pressure (700 Torr). After 21 hours, the calculated amount of SO$_2$F$_2$ (87.7 grams, 0.86 moles) had all been added and the reactor pressure was 347 Torr. No solids were observed in the head space. The flask was then equipped for vacuum distillation and the solvent and some base was distilled off (1.6 Torr, 65° C. bath, 53° C. head). The flask contents (203 grams), a clear yellow oil, were then slowly poured into a stirred solution of tetrabutylammonium bromide (161 g, 0.5 mole) in warm water (1.5 Kg). The solid so obtained was suction filtered, compressed with a rubber dam, and dissolved in hot methanol. The solution was polish filtered, diluted with water (40 mL), brought to a total volume of 1 liter while hot, and cooled to −25° C. The crystals so obtained were collected by filtration and dried at 45° C. in a vacuum oven to constant weight. Yield, 154.3 grams (0.36 moles, 85%), mp=97-99° C.

Example 2

A 2 liter stainless steel reactor (Parr Instrument Company, Moline, Ill.) was charged with ACS grade ammonium fluoride (NH$_4$F, 36.2 g, 0.98 mole), TMPDA (327 g, 2.5 mole) and acetonitrile (842 g). The reactor was sealed and evacuated to a pressure of 57 Torr and thereafter stirring commenced. Sulfuryl fluoride (208.8 g, 2.05 mol) was added continuously at a set pressure between 650 and 750 Torr with moderate stirring. The temperature slowly rose from 12° C. to 25° C. and a temperature of 25-27° C. maintained throughout the remainder of the SO$_2$F$_2$ addition, about 24 h. The excess gases were pumped out and the reactor opened. No solids were found in the reactor head space. The contents were saturated with ammonia gas and the resulting solid filtered off and washed with acetonitrile. The combined filtrates were concentrated to a clear yellow oil (306 g) and treated with tetrabutylammonium bromide as before, to give the product from methanol in two crops, 360.6 g (0.85 mole, 87%), m.p.=98.5-99.5° C.

Example 3

A 2 liter stainless steel reactor was charged with TMPDA (375 g, 2.88 moles) and acetonitrile (750 g), cooled to −10° C., and evacuated to 19 Torr with stirring. The reactor was then equilibrated with SO$_2$F$_2$ to a gated pressure of 70 Torr and ammonia gas (23.4 g, 1.37 mole) introduced over a period of 2 hours at this pressure and temperature. At the end of the ammonia addition, 117 g (1.15 moles) of SO$_2$F$_2$ had been added. The temperature of the reactor was then raised to 25° C. and an additional 165 g SO$_2$F$_2$ added at a pressure of 250-500 Torr and the reactor contents stirred overnight. Excess gas was pumped off and the reactor opened. A small amount of solid was observed on the exposed cooling coils but the head space was otherwise free of solids. The product was treated with tetrabutylammonium bromide as before and worked up to give a single crop of product (487 g, 1.15 moles, 84%), mp=97-101° C.

Comparative Example 1

A 2 liter stainless steel reactor (Parr Instrument Company, Moline, Ill.) was charged with ammonium chloride (NH$_4$Cl, 43 g, 0.8 mole), TMPDA (259 g, 1.99 mole) and acetonitrile (838 g). The reactor was sealed and evacuated to a pressure of 122 Torr and thereafter stirring commenced. The reactor was brought to 25° C. and sulfuryl fluoride (162.4 g, 1.59 mol) was added continuously at a set pressure between 650 and 750 Torr with moderate stirring at 25-27° C. over 18 h. The excess gases were pumped out and the reactor was opened. The reactor head space had some accumulated solids at the interface. A quantity of settled solid was filtered off and washed with acetonitrile. The combined filtrates were concentrated to a clear yellow oil (321 g) and treated with tetrabutylammonium bromide as before, to give the product from methanol. Only one crop was collected (226 grams) with an extended melting range of 98-120+° C., indicative of contamination.

Comparative Example 2

A two-gallon (7.57 L) stainless steel high pressure reactor (Parr Instrument Company, Moline, Ill. USA) was charged with acetonitrile (3.72 kg) and tetramethyl-1,3-propanediamine (TMPDA, 1.50 kg, 11.5 moles). The reactor was evacuated with medium stirring until a static vacuum of 43-45 Torr at 10° C. persisted for at least ten minutes. Sulfuryl fluoride ($SO_2F_2$) was introduced to the reactor through a pressure-gated dip tube until the setpoint pressure of 760 Torr was achieved. At the end of the addition, a total of 227.5 g $SO_2F_2$ had been added, and the reactor temperature rose from 11° C. to 14° C. The stir rate was then set to 80% of maximum and $NH_3$ gas (96 g, 5.63 moles) was added at a constant rate over a three hour period, allowing the temperature to rise to 23-25° C., then cooled as necessary to maintain this temperature range. $SO_2F_2$ addition at the setpoint pressure was continuous throughout this time. After the $NH_3$ addition was complete, $SO_2F_2$ addition continued until the theoretical weight (1.14 kg, 11.2 moles) had been added. The reactor was then stirred at a reduced rate for ten hours; the pressure dropped from 760 to 123 torr and the temperature from 25° C. to 15° C. during this time. The reactor contents, a clear, light yellow liquid, were transferred via the dip tube to a large rotary evaporator under reduced pressure and the sealed reactor washed with 1 kg acetonitrile, again through the dip tube. Concentration of the combined liquors at 60 C/150 torr to 60 C/80 torr gave 2.886 kg of a viscous liquid residue, which was added at a constant rate over 14 minutes to a vigorously stirred solution of tetrabutylammonium bromide (2 kg, 6.2 mole) in warm (31° C.) water (10 Kg). The glass receptacles were washed with 3×25 mL methanol and added to the stirred pot. The pot was stirred an additional 20 minutes. The solid so obtained was collected by suction filtration and compressed with a rubber dam. The damp solid (3.245 kg) was taken up in warm methanol (4.93 kg), polish filtered, and cooled to −20° C. The crystalline product was collected by filtration, the cake rinsed twice with chilled methanol, and dried at 45° C. in dynamic vacuum to constant weight. Yield, 1.992 kg (4.71 moles, 84.4%) of a white crystalline product; m.p.=97° C. to 99° C. A second crop (208.2 g, 0.49 mole, 8.8%), m.p.=97° C. to 99° C., was obtained by concentration of the filtrate. The remaining filtrate was combined with the aqueous residue from the initial isolation of the product and further rotovapped down at 60° C. The solid mass which resulted was separated and recrystallized from methanol as before, yielding a third crop (44.6 g, 0.1 mole, 1.9%), m.p.=97° C. to 99° C. Total yield, 2.245 kg (5.31 moles, 95.1%). The reactor was opened after transfer of the contents and extensive deposition of solids in the reactor head space, inlet pipes, and check valves were found.

These examples illustrate possible embodiments of the present invention. While various embodiments of the present invention have been described above, it should be understood that these are presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A process for the production of a salt of bis(fluorosulfonyl) imide anion ($M^{x+}_m[(FSO_2)_2N^-]_n$, wherein $M^+$ is an inorganic or organic cation and x, n and m are integers from 1-4, comprising:
    adding ammonia ($NH_3$) to a solution of sulfuryl fluoride ($SO_2F_2$) in a solvent in a sealed reactor, in the presence of an aprotic base, while maintaining a pressure inside the sealed reactor below 0.01 MPa (75 Torr), to produce a solution or concentrate comprising the product ion $[(FSO_2)_2N]^-$ ("FSI");
    mixing the solution comprising the product ion $[(FSO_2)_2N]^-$ ("FSI") to a solution or concentrate comprising of a salt of $M^{x+}$ and
    isolating the resulting salt comprising bis(fluorosulfonyl) imide anion ($[(FSO_2)_2N]^-$).

2. The process of claim 1, in which the solvent, the aprotic base and an initial amount of sulfuryl fluoride ($SO_2F_2$) are mixed in a sealed reactor to form a solution comprising an initial amount of sulfuryl fluoride ($SO_2F_2$) before adding ammonia.

3. The process of claim 1, wherein the solution comprises a solvent selected from the group consisting of acetonitrile, propionitrile, butyronitrile, diethyl ether, tetrahydrofuran, dimethylformamide, dimethylacetamide, N-methylpyrollidinone, tetramethylurea, dimethylpropyleneurea, dimethylethyleneurea and combinations thereof.

4. The process of claim 1, wherein the aprotic base is N,N,N',N'-tetramethyl-1,3-propanediamine.

5. The process of claim 1, wherein the ammonia is added through slow infusion of ammonia gas into the solution.

6. The process of claim 1, wherein a pre-determined stoichiometry of ammonia ($NH_3$) to $SO_2F_2$ is in a molar ratio in the range from about 1:3 to about 1.1:2.

7. The process of claim 1, comprising agitating the solution at a temperature in the range from −30° C. to 40° C. during the addition of ammonia.

8. The process of claim 1, wherein the salt having the formula $([M]^{x+})_m([(FSO_2)_2N]^+)_n$ is isolated as a solid, and is collected by filtration.

9. The process of claim 1, wherein the organic salt is dissolved in a biphase-forming solvent, and the salt having the formula $([M]^{x+})_m([(FSO_2)_2N]^-)_n$ comprises one layer of the resulting biphasic liquid.

10. A process for the production of a salt of bis(fluorosulfonyl) imide anion ($Mx^{x+}_m[(FSO_2)_2N^-]_n$, wherein $M^+$ is an inorganic or organic cation and x, n and m are integers from 1-4, comprising,
    adding ammonia ($NH_3$) to a solution comprising an initial amount of sulfuryl fluoride ($SO_2F_2$) in a solvent in a sealed reactor, in the presence of an aprotic base, while maintaining a pressure inside the sealed reactor below 0.01 MPa (75 Torr);
    continuously adding an additional amount of sulfuryl fluoride ($SO_2F_2$) after the step of adding ammonia is complete, at a pressure greater than 0.008 MPa, until a pre-determined stoichiometry has been reached to form a dissolved [(FSO2)2N]⁻ anion and a dissolved fluoride anion;

optionally distilling off the solvent; and isolating a salt comprising the [(FSO$_2$)$_2$N⁻] anion.

11. The process of claim 10, wherein the ammonia is added through slow infusion of ammonia gas into the solution comprising an initial amount of sulfuryl fluoride (SO$_2$F$_2$).

12. The process of claim 10, wherein the step of isolating the resulting salt comprises adding a solution of a salt comprising an organic cation.

13. A process for the production of a salt of bis(fluorosulfonyl) imide anion $(M^{x+}{}_m[(FSO_2)_2N^-]_n$, wherein M⁺ is an inorganic or organic cation and x, n and m are integers from 1-4, comprising:

adding sulfuryl fluoride (SO$_2$F$_2$) to a suspension, pellet, or other form of solid ammonium fluoride in a solvent in a sealed reactor, in the presence of an aprotic base, wherein the pressure within said sealed reactor is below 0.01 MN (75 torr) after ammonium fluoride is added; and isolating said salt.

14. The process of claim 13, wherein the step of adding ammonium fluoride to a solution comprising sulfuryl fluoride (SO$_2$F$_2$) comprises providing solid ammonium fluoride to a solvent in a sealed reactor;

providing an aprotic base and an initial amount of sulfuryl fluoride (SO$_2$F$_2$) in a sealed reactor; and continuously adding an additional amount of SO$_2$F$_2$ to reach a pre-determined stoichiometry while maintaining a pressure inside the sealed reactor at or below about 0.3 MPa.

15. The process of claim 13, further comprising applying vacuum to the sealed reactor.

16. The process of claim 13, wherein the solvent is selected from the group consisting of acetonitrile, propionitrile, diethyl ether, tetrahydrofuran, butyronitrile, dimethylformamide, dimethylacetamide, N-methylpyrollidinone, tetramethylurea, dimethylpropyleneurea, dimethylethyleneurea and a combinations thereof.

17. The process of claim 13, wherein the aprotic base is N,N,N',N'-tetramethyl-1,3-propanediamine.

18. The process of claim 13, wherein the pre-determined stoichiometry of ammonium fluoride to SO$_2$F$_2$ is in a molar ratio in the range from 1:3 to 1.1:2.

19. The process of claim 13, wherein the reaction is maintained at a temperature in the range from −30° C. to +50° C. during the step of adding sulfuryl fluoride (SO$_2$F$_2$).

20. The process of claim 13, wherein the step of isolating the resulting salt comprises adding a solution of a salt comprising an organic cation.

* * * * *